US005630807A

United States Patent [19]
Joffe

[11] Patent Number: 5,630,807
[45] Date of Patent: May 20, 1997

[54] SUCTION DEVICE WITH JET BOOST

[76] Inventor: Michael Joffe, 25 Alderbrook, Wrentham, Mass. 02093

[21] Appl. No.: 601,327

[22] Filed: Feb. 16, 1996

[51] Int. Cl.$^6$ .............................. A61M 1/00; B01D 19/00
[52] U.S. Cl. .................. 604/315; 604/313; 604/317; 55/467
[58] Field of Search .................... 604/313, 315–317, 604/320, 319; 55/385.1, 467, 35, 118; 128/303.1, 747

[56] References Cited

U.S. PATENT DOCUMENTS

| | | | |
|---|---|---|---|
| 4,450,756 | 5/1984 | Kling | 55/467 |
| 4,735,603 | 4/1988 | Goodson et al. | 604/317 |
| 4,921,492 | 5/1990 | Schultz et al. | 604/315 |
| 4,963,134 | 10/1990 | Backscheider et al. | 55/467 |
| 5,009,685 | 4/1991 | Wilson et al. | 55/467 |
| 5,015,243 | 5/1991 | Schifano | 604/315 |
| 5,047,072 | 9/1991 | Wertz et al. | 604/317 |
| 5,322,521 | 6/1994 | Wilk | 604/317 |

*Primary Examiner*—John G. Weiss
*Assistant Examiner*—David J. Cho
*Attorney, Agent, or Firm*—John R. Ross

[57] ABSTRACT

A device for evacuating ablation products of tissue ablated with a pulse laser beam. A gas is forced through at least one compressed gas jet nozzle. An evacuation nozzle is spaced apart from the compressed gas jet nozzle and a pulse laser beam passes in between the jet nozzle and the evacuation nozzle to illuminate and ablate tissue. A vacuum system provides a vacuum at the evacuation nozzle sufficient to provide a vacuum mass flow rate substantially greater than the compressed gas mass flow rate so that the products of the ablation are entrained in gas exiting the gas jet nozzles and evacuated along with the gas through the evacuation nozzle.

11 Claims, 2 Drawing Sheets

PRIOR ART

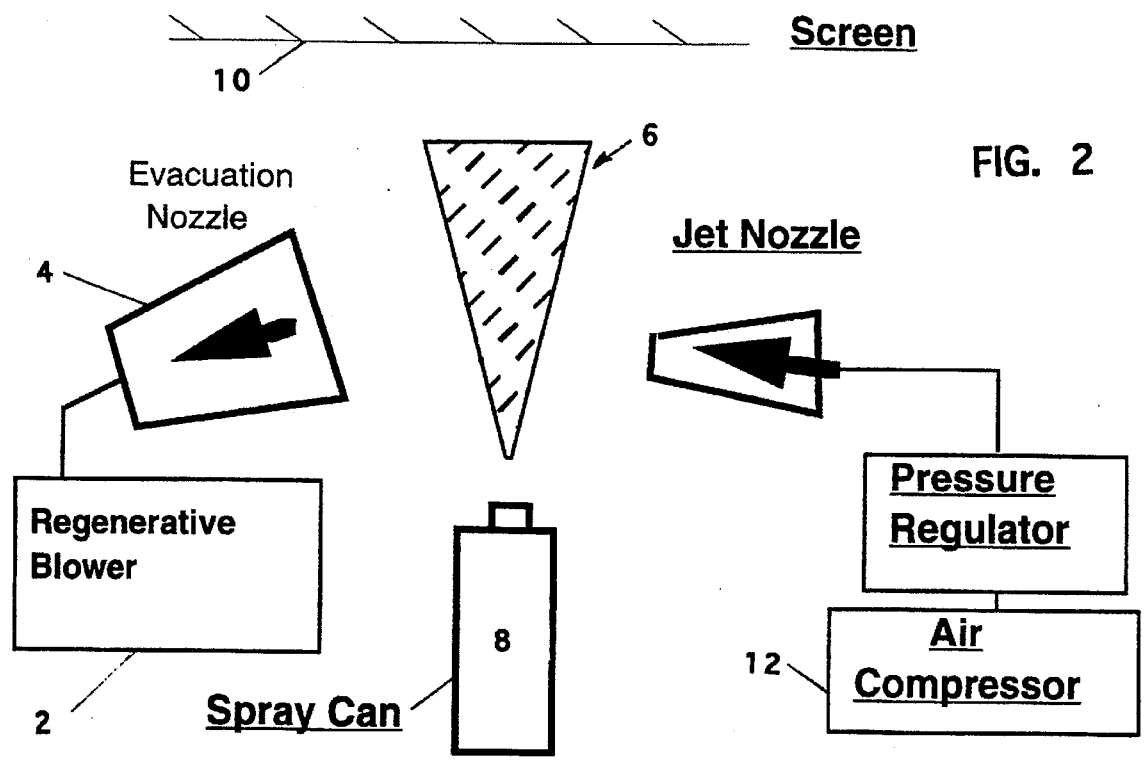
FIG. 2
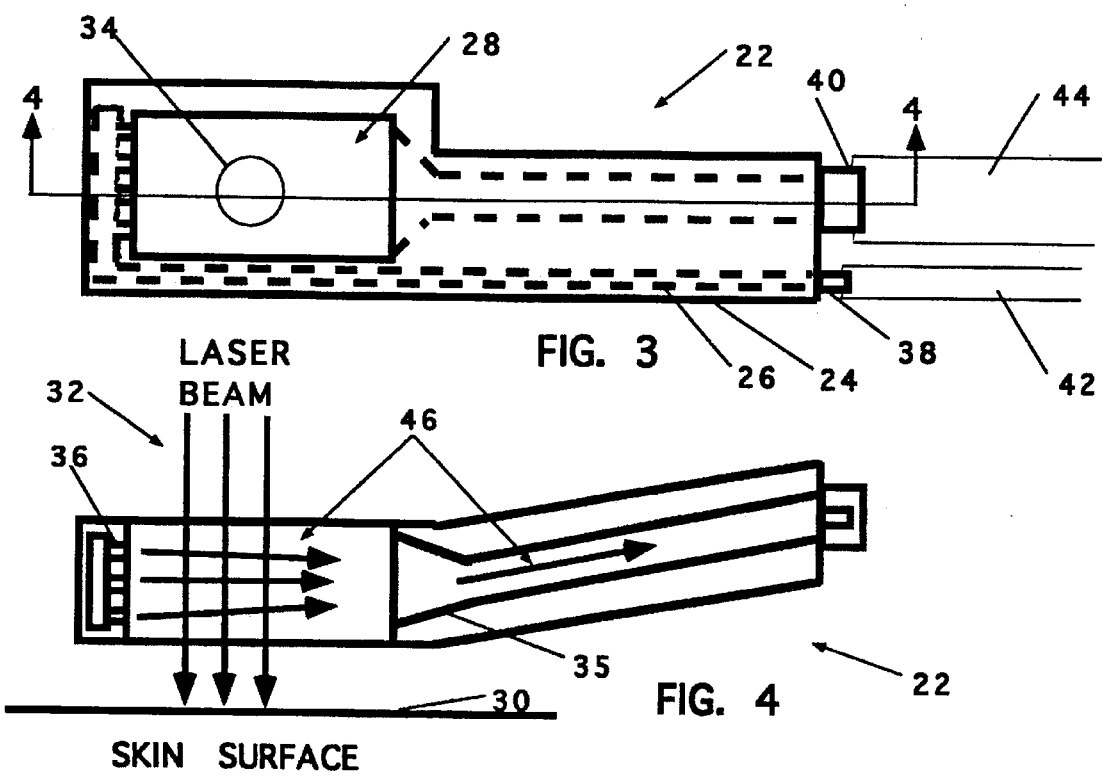
FIG. 3
FIG. 4

SUCTION DEVICE WITH JET BOOST

This invention relates to suction devices and in particular to suction devices for use in laser surgery.

BACKGROUND OF THE INVENTION

When lasers are used in surgery, tissue is often ablated producing smoke and vaporized tissue. This smoke and vaporized tissue is potentially dangerous and can contaminate delicate medical equipment. It is standard practice for an assistant to the surgeon to remove the products of the ablation with a suction device. Laser plumes consist of microscopic particles flying ballistically away from the irradiated tissue surface. The idea of suction, as shown in FIG. 1A, is to impart to the plume particle a velocity component parallel to the surface in the direction of the suction nozzle so that it can be captured inside a suction nozzle. The larger the horizontal velocity component, the more efficient suction is. A 5 µm diameter, $5 \times 10^{-10}$ g particle, initially flying ballistically vertically with a velocity V and subject to a horizontal wind U, will have a trajectory roughly equal to:

$$z = (0.1) V \sqrt{\frac{x}{U}},$$

where z and x are respectively the particle's vertical and horizontal components.

FIG. 1B shows plots of a the trajectory of the 5 µm particle assuming a 100 cm/s initial velocity for 5 different horizontal wind velocities.

In order to remove all of the products of ablation, the mouth of a suction device typically must be held close to the location of the surgery; however, use of the suction device close to the surgery area can be disruptive to the surgery.

SUMMARY OF THE INVENTION

The present invention provides a device for evacuating plume products. A gas is forced through at least one compressed gas jet nozzle which directs a compressed gas flow toward an evacuation orifice. A vacuum system provides a vacuum at said evacuation orifice sufficient to provide a vacuum mass flow rate substantially greater than said compressed gas mass flow rate so that the plume products are entrained in gas exiting said gas jet nozzles and evacuated along with the gas through the evacuation orifice. The device is especially useful in laser surgery to evacuate ablation products in plumes created by pulse lasers.

BRIEF DESCRIPTION OF THE DRAWINGS

FIG. 2 shows the elements of a demonstration of the principals of the present invention.

FIG. 3 shows the top elevation of the elements of a preferred embodiment of present invention.

FIG. 4 shows the side elevation of the elements of a preferred embodiment of present invention.

DETAILED DESCRIPTION OF PREFERRED EMBODIMENTS

Figure 1A:
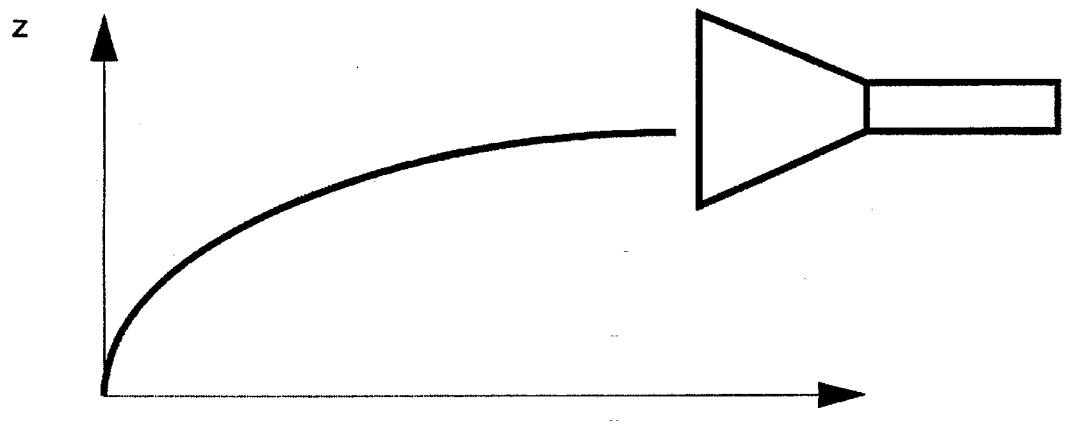
FIG. 1A illustrates typical prior art suction devices.
Figure 1B:
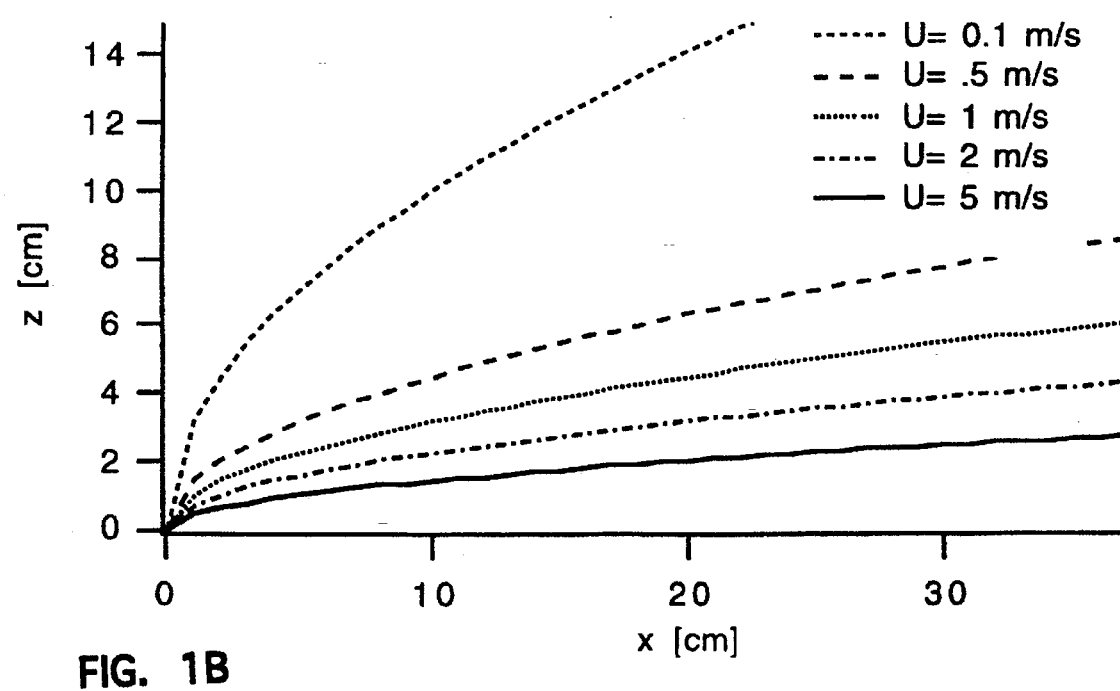
FIG. 1B shows a plot of a typical plume particle subject to various horizontal winds.

As can be seen from FIG. 1B, in order for the trajectory of the plotted particles to end inside a typical 1 cm sized nozzle located 10 cm away, the wind velocity has to exceed 5 m/s. It is impossible to achieve this air flow with suction nozzles. Typical suction velocities are in the range of 0.25 to 0.75 m/s. However, it is very easy to create air velocities of 5 m/s with a blower or compressed air.

Demonstration

I conducted a simple demonstration to illustrate the principles of my invention. The elements of the demonstration are shown in FIG. 2. Blower 2 with suction nozzle 4 was completely ineffective in preventing paint spray plume 6 from paint spray can 8 from reaching screen 10. However, when compressed air from air compressor 12 was directed at spray plume 6 in the direction of suction nozzle 4, essentially all of the spray was sucked into suction nozzle 4 and none of the spray reached screen 10.

Preferred Embodiment

A preferred embodiment of the present invention can be described by reference to FIGS. 3 and 4.

A preferred embodiment of a suction device with a jet spray can be described by reference to FIGS. 3 and 4. The suction device 22 has a shape generally similar to a frame of a tennis racket. A handle 24 provides a compressed air passage 26 for incoming compressed air and an exhaust passage for evacuation of the compressed air and a laser created plume. Suction device 22 provides a rectangular illumination space 28 through which skin surface 30 is illuminated by laser beam 32 at spot 34. The plume created by the ablation of skin tissue is blown toward evacuation nozzle 35 by compressed air exiting at high speed from 12 compressed air jet nozzles 36.

Suction device 22 is comprised of molded plastic with standard fittings 38 and 40 to accommodate flexible compressed air hose 42 and flexible vacuum hose 44. A compressor (e.g. Gast Model 1531-107B-G557X) with a regulator capable of providing compressed air at about 1 liter/min at 100 psi is connected to the suction device with hose 42. Compressed air enters device 22 through fitting 38 and exits through 12 jet nozzles 36, each about 0.5 mm diameter. At 1 litter/min, air exits nozzles 36 with velocity of about 5 to 10 m/s, which is sufficient for imparting significant drag force to plume particles created by laser pulses 32 at spot 34. The air path is shown at 46

Evacuation hose 44 with an inside diameter of about 1 inch connects the device to a vacuum pump such as Gast Model R2103. Sufficient air moving capacity insures that the jet flow from nozzles 36 is only a small fraction of the total air flow through hose 44. Evacuation nozzle 46 is 4 cm high and 2.5 cm wide. Applicant's experiments have shown that essentially all plume particles and smoke are caught up in the compressed air flow and evacuated through exhaust nozzle 35.

In another preferred embodiment the suction device is incorporated as a feature of the laser optic at the terminal of a laser articulated arm. This permits the laser practitioner to operate without an assistant.

While the above description contains many specificities, the reader should not construe these as limitations on the scope of the invention, but merely as exemplifications of embodiments thereof. Those skilled in the art will envision many other possible variations which are within its scope. For example instead of a compressor, compressed gas in a compressed gas bottle can be used to provide the compressed gas to the compressed gas jet nozzle. Several jet nozzles could be provided with all of the nozzles focused on the evacuation nozzle. The present invention may in addition to laser surgery be used to capture other plumes such as those resulting from welding, soldering and brazing. A further improvement in the laser surgery device would be to cool the compressed gas to provide a therapeutic effect on the skin. The jet could be synchronized with the laser pulse to save on compressed air, reduce suction requirements and increase collection efficiency by means of a shock wave front. Cooling the compressed air could also generate mist due to moisture condensation. Water droplets and snowflakes can then transfer momentum to plum particles and impart greater drag force than mere air. A mist can be added to the compressed air jet with a special spraying nozzle. (In all of these embodiments utilizing water droplets, the effect on the laser beam must be considered and it might be necessary to increase the energy in the laser beam. In another embodiment a disinfecting agent can be added to the compressed gas to help eliminate microorganisms in the plume. Also a deodorizing agent could be added to reduce odors. A built in filter can be added to the suction portion of the device. A tank or other appropriate accumulator could be provided for accumulation of the plume products. Alternately, the plume products could be directed outdoors when this is permitted. With appropriate arrangement of piping, filter and waste accumulator tank a single compressor could be used to provide both compressed gas for the jet nozzle and the suction for the suction orifice. Accordingly, the reader is requested to determine the scope of the invention by the appended claims and their legal equivalents and not by the examples which have been given.

I claim:

1. A plume suction device for evacuating plume products produced in an open air operation, said device comprising:
   a) at least one evacuation orifice;
   b) at least one compressed gas jet nozzle spaced apart from said at least one evacuation orifice and located so as to direct compressed gas toward said evacuation orifice;
   c) a compressed gas source means for providing a compressed gas flow defining a compressed gas mass flow rate to said at least one compressed gas jet nozzle, wherein said device is configured to contain plumes produced by a pulse laser and further comprising a synchronizing compressed gas control means for synchronizing said compressed gas flow with pulses from said pulse laser, and
   d) a suction means for providing a vacuum mass flow rate through said evacuation orifice substantially greater than said compressed gas mass flow rate,
   wherein said plume suction device when positioned with said evacuation orifice and said jet nozzle on opposite sides of a plume, products of said plume are entrained in gas exiting said gas jet nozzle and evacuated along with said gas through said evacuation orifice.

2. The plume suction device as in claim 1 wherein said compressed gas source is an air compressor.

3. The plume suction device as in claim 1 wherein said compressed gas source is a compressed gas bottle.

4. The plume suction device as in claim 1 wherein said at least one compressed gas nozzle is a plurality of compressed gas nozzles.

5. The plume suction device as in claim 1 and further comprising a cooling means to cool said compressed gas.

6. The plume suction device as in claim 1 and further comprising a filter for capturing products contained in said plume.

7. The plume suction device as in claim 1 and further comprising a disinfecting means for adding a disinfectant to said compressed gas flow.

8. The plume suction device as in claim 1 and further comprising a deodorant means for adding a deodorant to said compressed gas flow.

9. The plume suction device as in claim 1 and further comprising a tank means for collecting products of said plume.

10. The plume suction device as in claim 1 and further comprising a hose means for conveying products of said plume outdoors.

11. The plume suction device as in claim 1 wherein said compressed gas source and said suction means comprises a single air compressor.

* * * * *